(12) United States Patent
Haas et al.

(10) Patent No.: US 7,867,445 B1
(45) Date of Patent: *Jan. 11, 2011

(54) EXPLOSIVES TESTER

(75) Inventors: Jeffrey S. Haas, San Ramon, CA (US); Douglas E. Howard, Livermore, CA (US); Joel D. Eckels, Livermore, CA (US); Peter J. Nunes, Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1204 days.

This patent is subject to a terminal disclaimer.

(21) Appl. No.: 10/788,558

(22) Filed: Feb. 26, 2004

Related U.S. Application Data

(63) Continuation-in-part of application No. 10/610,904, filed on Jun. 30, 2003, now Pat. No. 7,294,306.

(51) Int. Cl.
*G01N 33/00* (2006.01)
(52) U.S. Cl. .......................... 422/68.1; 422/55; 422/56; 422/57; 422/58; 422/99; 422/103; 422/104
(58) Field of Classification Search .................. 422/50, 422/55–58, 68.1, 99, 103, 104
See application file for complete search history.

(56) References Cited

U.S. PATENT DOCUMENTS

| | | | |
|---|---|---|---|
| 4,496,520 A * | 1/1985 | Heller et al. .................. 422/60 |
| 4,554,133 A | 11/1985 | Leichnitz | |
| 4,783,316 A | 11/1988 | Pannwitz | |
| 4,788,039 A * | 11/1988 | Glattstein ..................... 422/61 |
| 5,035,860 A * | 7/1991 | Kleingeld et al. ............. 422/61 |
| 5,035,862 A * | 7/1991 | Dietze et al. ................ 422/68.1 |
| 5,138,889 A * | 8/1992 | Conrad ..................... 73/863.12 |
| 5,310,681 A | 5/1994 | Rounbehler et al. | |
| 5,551,278 A | 9/1996 | Rounbehler et al. | |
| 5,638,166 A | 6/1997 | Funsten et al. | |
| 5,648,047 A * | 7/1997 | Kardish et al. ................. 422/56 |
| 5,679,584 A | 10/1997 | Mileaf et al. | |
| 5,912,466 A | 6/1999 | Funsten et al. | |
| 6,245,576 B1 | 6/2001 | Hiley | |
| 6,406,918 B1 | 6/2002 | Bannister et al. | |
| 6,470,730 B1 | 10/2002 | Chamberlain | |
| 6,477,907 B1 | 11/2002 | Chambers et al. | |
| 2005/0287036 A1* | 12/2005 | Eckels et al. ................... 422/61 |

OTHER PUBLICATIONS

Yinon, J., et al., "The Analysis of Explosives," Pergamon Press, 1981, 73 pages.

Parker, R.G., et al., "Analysis of Explosives and Explosive Residues. Part 1: Chemical Tests," Journal of Forensic Sciences, vol. 20, No. 1, 1975, pp. 133-140.

(Continued)

*Primary Examiner*—Sam Siefke
(74) *Attorney, Agent, or Firm*—Eddie E. Scott; James S. Tak

(57) ABSTRACT

An explosives tester that can be used anywhere as a screening tool by non-technical personnel to determine whether a surface contains explosives. First and second explosives detecting reagent holders and dispensers are provided. A heater is provided for receiving the first and second explosives detecting reagent holders and dispensers.

12 Claims, 5 Drawing Sheets

OTHER PUBLICATIONS

Thornton, J.I., "The Chemistry of Death by Gunshot," Analytica Chimica Acta 288 (1994) Elseiver Science B.V., pp. 71-81.

Crockett, A.B., et al., "Field Sampling and Selecting On-Site Analytical Methods for Explosives in Soil," EPA Federal Facilities Forum Issue, EPA/540/R-97/501, Nov. 1996, pp. 1-33.

Crockett, A.B., et al., Field Sampling and Selecting On-Site Analytical Methods for Explosives in Soil, EPA Project Summary, EPA/540/S-97/501, Dec. 1996, pp. 1-9.

Mamginell, R. P., et al., Finite Element Modeling of a Microphotplate for Microfluidic Applications, Presented at MEMs99, Sandia National Laboratories, Harvard Thermal Inc., 1999, 6 pages.

Beveridge, A., "Forensic Investigation of Explosions," Taylor & Francis, Defense Research Agency, Farnborough, Hants GU14 6TD UK, 1993, 13 pages.

Meng, H., et al., "Gunshot Residue Analysis—A Review," Journal of Forensic Sciences, 42(4), 1997, pp. 553-570.

Fox, J. B., Jr., "Kinetics and Mechanisms of the Griess Reaction," Analytical Chemistry, vol. 51, No. 9, Aug. 1979, 14 pages.

Nam, S., et al., "On-Site Analysis of Explosives in Soil: Evaluation of Thin-Layer Chromatography for Confirmation of Analyte Identity," U.S. Army Environmental Center, Aberdeen Proving Ground, MD, 2000, 4 pages.

Nam, S., "On-Site Analysis of Explosives in Soil: Evaluation of Thin-Layer Chromatography for Confirmation of Analyte Identity," U.S. Army Environmental Center, U.S. Army Corps of Engineers, Special Report 97-21, Aug. 1997, 20 pages.

Jenkins, T. F., et al., "On-Site Analysis for High Concentrations of Explosives in Soil Extraction Kinetics and Dilution Procedures," U.S. Army Environmental Center, U.S. Army Corps of Engineers, Special Report 96-10, May 1996, 18 pages.

Krishnamurthy, R., et al., "Simultaneous Detection of High Explosives in Post-Explosion Debris by HPTLC with Two Successive Mobile Phases," Journal of Planar Chromatography, vol. 12, Sep./Oct. 1999, pp. 394-397.

Peak, S.A.., "A Thin-Layer Chromatographic Procedure for Confirming the Presence and Identity of Smokeless Powder Flakes," Journal of Forensic Sciences, vol. 25, No. 3, Jul. 1980, pp. 679-681.

Douse, J.M.F., et al., "Trace Analysis of Explosives and Firearm Discharge Residues in the Metropolitan Police Forensic Science Laboratory," Metropolitan Police Forensic Science Laboratory, London, UK, Journal of Energetic Materials, vol. 4, 1986, pp. 169-188.

Grant, P., "Chemistry Field Assets Instruments & Otherwise," Iraq Planning Meeting, Albuquerque, NM, Lawrence Livermore National Laboratory Forensic Science Center, Aug. 2002, 4 pages.

Jenkins, T., et al., "Development of Field Screening Methods for TNT, 2,4-DNT and RDX in Soil," Geological Sci., Talonia, vol. 39, No. 4, pp. 419-428, Pergamon Press, 1992.

Hiley, R., "Investigations of Thin Layer Chromatographic Techniques Used for Forensic Explosives Analysis in the Early 1970s," Hiley—TLC Techniques for Explosives Analysis, Journal of Forensic Sciences, Jul. 1993, pp. 864-873.

Fetterolf, D., "Portable Instrumentation: New Weapons in the War Against Drugs and Terrorism," SPIE, vol. 2092, 1993, pp. 40-52.

Twibell, J., et al., "The Persistence of Military Explosives on Hands," Journal of Forensic Sciences, vol. 29, No. 1, Jan. 1984, pp. 284-290.

Haas, J., et al., "Thin-Layer Chromatography (TLC) Analysis of Exhumed MMR Ordnance," Lawrence Livermore National Laboratory Forensic Science Center, Sep. 1998, 9 pages.

Twibell, J., et al., "Transfer of Nitroglycerine to Hands During Contact with Commercial Explosives," Journal of Forensic Sciences, vol. 27, No. 4, Oct. 1982, pp. 783-791.

Andresen, B., et al., "Recent Innovations for the Detection of Propellant Stabilizers and HE in the Field," 2000 Global Demilitarization Symposium & Exhibition, National Defense Industrial Association, Event #058, Coeur d'Alene, ID, May 2000, 20 pages.

* cited by examiner

EXPLOSIVES TESTER

CROSS-REFERENCE TO RELATED APPLICATIONS

This application is a Continuation-In-Part (CIP) of U.S. patent application Ser. No. 10/610,904 entitled "Inspection Tester for Explosives," filed on Jun. 30, 2003 now U.S. Pat. No. 7,294,306 by Jeffrey S. Haas, Randall L. Simpson, and Joe H. Satcher. The disclosure of U.S. patent application Ser. No. 10/610,904 entitled "Inspection Tester for Explosives," filed on June 30, 200 by Jeffrey S. Haas, Randall L. Simpson, and Joe H. Satcher is incorporated herein in its entirety by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to testing and more particularly to an explosives tester.

2. State of Technology

U.S. Pat. No. 5,638,166 for an apparatus and method for rapid detection of explosives residue from the deflagration signature thereof issued Jun. 10, 1997 to Herbert O. Funsten and David J. McComas and assigned to The Regents of the University of California provides the following state of the art information, "Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. See, Fetterolf et al., Portable Instrumentation: New Weapons in the War Against Drugs and Terrorism," Proc. SPIE 2092 (1993) 40, Yinon and Zitrin, in Modern Methods and Applications in Analysis of Explosions, (Wiley, New York, 1993) Chap. 6; and references therein. Vapor detection is achieved using trained animals, gas chromatography, ion mobility mass spectrometry, and bioluminescence, as examples. All of these techniques suffer from the inherently low vapor pressures of most explosives. Bulk detection of explosives may be performed using x-ray imaging which cannot detect the explosives themselves, but rather detects metallic device components. Another method for bulk detection involves using energetic x-rays to activate nitrogen atoms in the explosives, thereby generating positrons which are detected. This technique requires an x-ray generator and a minimum of several hundred grams of explosives. Bulk detection is also accomplished using thermal neutron activation which requires a source of neutrons and a .gamma.-radiation detector. Thus, bulk detection is not sensitive to trace quantities of explosives and requires large, expensive instrumentation. Tagging requires that all explosives be tagged with, for example, an easily detected vapor. However, since tagging is not mandatory in the United States, this procedure is clearly not reliable. It turns out that there are no technologies for performing accurate, real-time (<6 sec) detection and analysis of trace explosives in situ. Only trained dogs can achieve this goal.

It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," J. Forensic Science 27 (1982) 783; J. D. Twibell et al., "The Persistence of Military Explosives on Hands," J. Forensic Science 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives.

U.S. Pat. No. 5,679,584 for a method for chemical detection issued Oct. 2, 1997 to Daryl Sunny Mileaf and Noe Esau Rodriquez, II provides the following state of the art information, "a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction."

U.S. Pat. No. 6,470,730 for a dry transfer method for the preparation of explosives test samples issued Oct. 29, 2002 to Robert T. Chamberlain and assigned to The United States of America as represented by the Secretary of Transportation provides the following state of the art information, "method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an explosives tester system. The explosives tester system can be used anywhere as a primary screening tool by non-technical personnel to determine whether a surface contains explosives. One embodiment of the present invention comprises an explosives tester system for testing for explosives associated with a test location. The system comprises a first explosives detecting reagent; a first reagent holder and dispenser, the first reagent holder and dispenser containing the first explosives detecting reagent; a second explosives detecting reagent, a second reagent holder and dispenser containing the second explosives detecting reagent; a sample collection unit for exposure to the test location, exposure to the first explosives detecting reagent, and exposure to the second explosives detecting reagent; and a environmental unit for receiving the sample collection unit and processing the sample collection unit for testing the test location for the explosives. In another embodiment, the explosives tester system comprises a body with a sample collection unit. A first reagent holder and dispenser is operatively connected to the sample collection unit. The first reagent holder and dispenser contains a first explosives detecting reagent (reagent A) and is positioned to deliver the first explosives detecting reagent to the sample collection unit. A second reagent holder and dispenser is operatively connected to the sample collection unit. The second reagent holder and dispenser contains a second explosives detecting reagent (reagent B) and is positioned to deliver the second explosives detecting reagent to the sample collection unit. A environmental unit for processing the sample collection unit for testing the test location for the explosives is operatively connected to the sample collection unit.

The explosives tester uses a simple and rapid method of operation. The collection unit is exposed to a suspect substance. This may be accomplished by the collection unit being swiped across a surface containing the suspect substance or the collection unit may be exposed to the suspect substance in other ways such as adding the suspect substance to the collection unit. The first reagent (reagent A) is deposited onto the collection unit with the suspect substance. If the collection unit becomes colored, it's positive for explosives. If no color appears then the additional steps are performed. In the next step, a heater is activated. If a color appears on the collection unit, the test positive for explosives. If no color appears then the additional step is performed. In the next step, the second reagent (reagent B) is a deposited onto the collection unit with the suspect substance. If the collection unit becomes colored, the test is positive for explosives. If no color appears then the test is negative for explosives.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
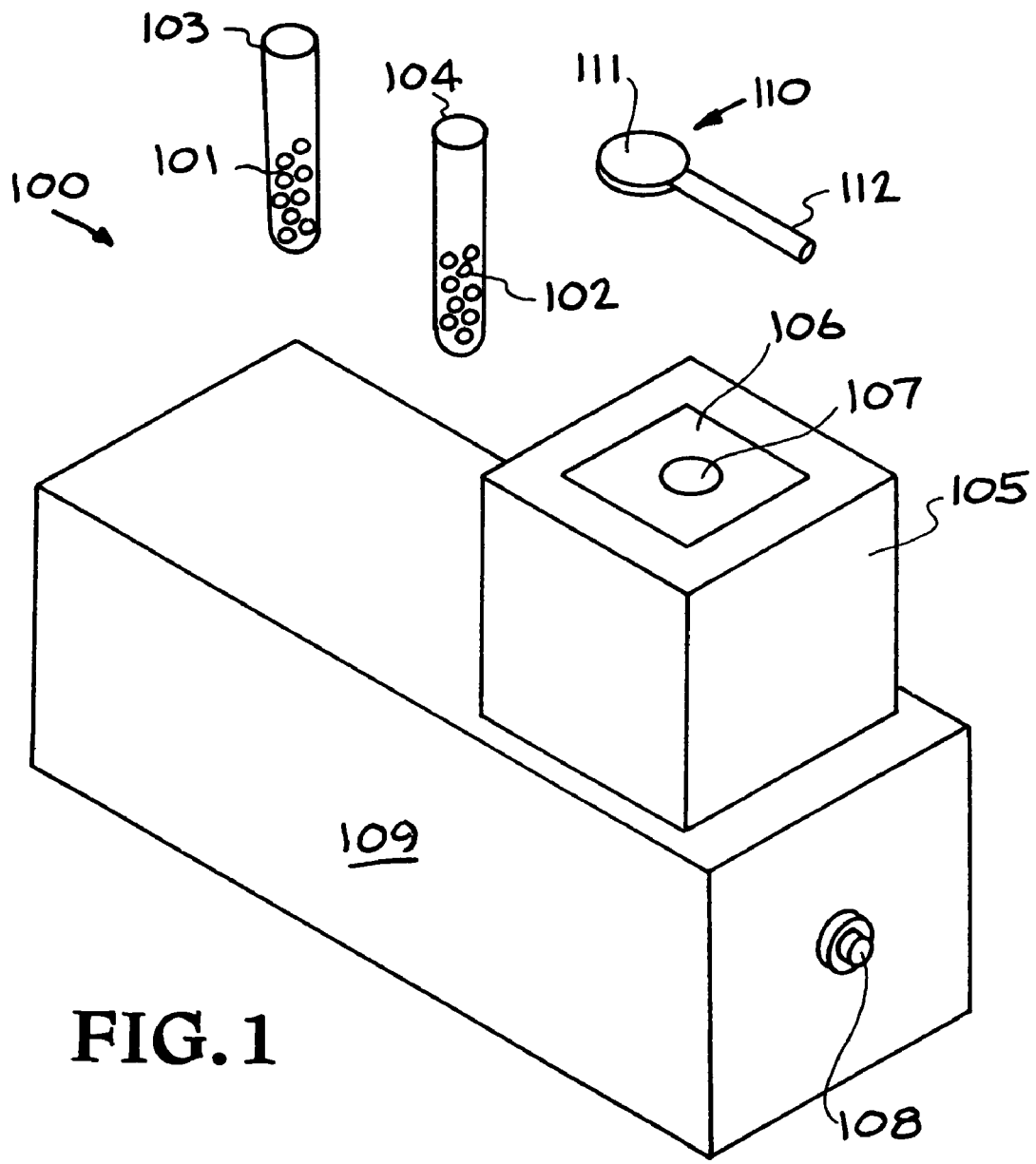
FIG. 1 illustrates a one embodiment of an explosives tester constructed in accordance with the present invention.

Referring now to the drawings and the following detailed description, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1 the drawings, an illustration of one embodiment of an explosives tester constructed in accordance with the present invention is illustrated. This embodiment of the explosives tester is designated generally by the reference numeral 100. The explosives tester 100 comprises a first explosives detecting reagent 101, a first reagent holder and dispenser 103, a second explosives detecting reagent 102, a second reagent holder and dispenser 104, containing said second explosives detecting reagent, a sample collection unit 110, and a heater 105 for receiving said sample collection unit 110. The first reagent holder and dispenser 103 contains and dispenses the first explosives detecting reagent 101. The second reagent holder and dispenser 104 contains and dispenses the second explosives detecting reagent 102. The heater 105 is positioned on a battery pack 109 that provides electrical power for the heater 105. The heater 105 includes a ceramic heating pad 106 and a receiving unit 107 for receiving the sample collection unit 110. A button switch 108 controls the battery pack 109 to turn the power on for a predetermined amount of time. Other types of heaters can be used for the heater 105, such as chemical heaters. In another embodiment the heater 105 is a chemical heater and the battery pack 109 is not included. Chemical heaters are well known in the art and need not be described here.

The structural details of embodiment of an explosives tester 100 for explosives constructed in accordance with the present invention having been described, the operation of the explosives tester 100 will now be considered. The explosives tester 100 uses a simple and rapid procedure summarized by the following four step operation:

STEP 1) A sample collection unit 110 is exposed to the suspect substance. This may be accomplished by the sample collection unit 110 being swiped across a surface containing the suspect substance or the sample collection unit 110 may be exposed to the suspect substance in other ways such as adding the suspect substance to the sample collection unit 110.

STEP 2) The first explosives detecting reagent 101 from first reagent holder and dispenser 103 is deposited onto the sample collection unit 110 with the suspect substance. If the sample collection unit 110 becomes colored, it's positive for explosives. If no color appears then the additional steps are performed.

STEP 3) The heater 105 is activated. The sample collection unit 110 is positioned in the receiving unit 107. The button switch 108 is pushed and the heater 105 is activated for a predetermined amount of time heating the ceramic pad 106 and the sample collection unit 110. If a color appears on the sample collection unit 110, it's positive for explosives. If no color appears then the additional step is performed.

STEP 4) The second explosives detecting reagent 102 from second reagent holder and dispenser 104 is deposited onto the sample collection unit 110 with the suspect substance. If the sample collection unit 110 becomes colored, it's positive for explosives. If no color appears then the test is negative for explosives.

Optional Additional Step—The heater 105 is activated. The sample collection unit 110 after is has been exposed to the second explosives detecting reagent 102 is positioned in the receiving unit 107. The button switch 108 is pushed and the heater 105 is activated for a predetermined amount of time heating the ceramic pad 106 and the sample collection unit 110. If a color appears on the sample collection unit 110, it's positive for explosives. If no color appears then the test is negative for explosives.

The particular embodiment of the explosives tester 100 uses reagents depending on the type of explosives present, the chemistry reaction scheme, the types of chemicals, the concentrations, the quantity, and the heat. A large number of common military and industrial explosives can be easily detected such as HMX, RDX, NG, TATB, Tetryl, PETN, TNT, DNT, TNB, DNB and NC. Many more compounds are being added to this list.

The explosives tester 100 is fast, sensitive, and is easy to implement. The explosives tester 100 can be used virtually anywhere, car portal checkpoints, airports, first responders, Federal, State, and local agencies. The explosives tester 100 can be used as a primary screening tool by non technical personnel to determine whether a surface contains explosives. Explosive Ordinance Disposal teams cannot simply explode suspect packages for concerns of disbursing radioactive material, biological agents, or chemical agents.

The particular embodiment of an explosives tester 100 will now be described in greater detail. As shown in FIG. 1 a swab 111 is attached to one end of a pencil sized wand 112 to provide the sample collection unit 110. The other end of the wand 112 serves as a handle. The swab 111 can be made of cotton, paper, polymer, or various other materials that will serve to retain and/or collect a sample. The wand 112 can be made of plastic, wood, metal, or various other materials. The swab 111 is attached to the wand by any suitable means such as glue, heating, crimping or various other means of attachment to provide the sample collection unit 110.

The sample collection unit is exposed to the first explosives detecting reagent 101. The first explosives detecting reagent 101 contains Meisenheimer complexes. Subsequently the sample collection unit 110 is exposed to the second explosives detecting reagent 102. The second explosives detecting reagent 102 provides a Griess reaction. The Meisenheimer complexes and Griess reaction are well known in the art and need not be described here.

The explosives testers 100 can be stored and carried in a case. The explosives tester for explosives 100 can be used virtually anywhere, car portal checkpoints, airports, first responders, Federal, State, and local agencies. A large number of common military and industrial explosives can be easily detected such as HMX, RDX, NG, TATB, Tetryl, PETN, TNT, DNT, TNB, DNB and NC.

Figure 2:
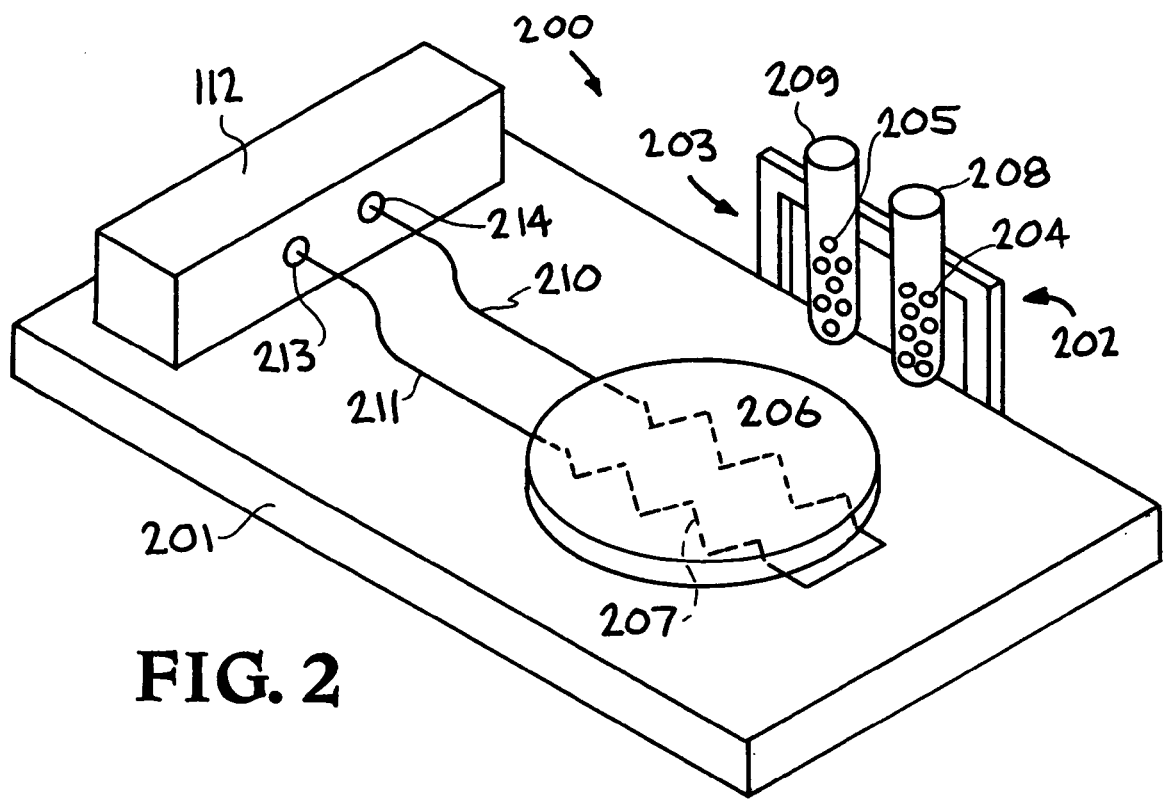
FIG. 2 illustrates another embodiment of an explosives tester constructed in accordance with the present invention.

Referring now to FIG. 2 another embodiment of an explosives tester for explosives constructed in accordance with the present invention is illustrated. This further embodiment is designated generally by the reference numeral 200. The explosives tester 200 comprises a body 201 with a sample collection unit 206 operatively connected to the body 201. A first explosives detecting reagent 204 (reagent A) is contained in a first reagent holder and dispenser 202 that is operatively connected to the body 201 and the sample collection unit 206.

The first reagent holder and dispenser 202 containing the first explosives detecting reagent 204 is positioned to deliver the first explosives detecting reagent 204 to the sample collection unit 206. A second explosives detecting reagent 205 (reagent B) is contained in a second reagent holder and dispenser 203 operatively connected to the body 201 and the sample collection unit 206. The second reagent holder and dispenser 203 containing the second explosives detecting reagent 205 is positioned to deliver the second explosives detecting reagent 203 to the sample collection unit 206. A heater 207 is operatively connected to the sample collection unit 206.

The sample collection unit in the embodiment 200 comprises a disk shaped cotton pad 206 that is attached to the body 201. The pad 206 can be made of cotton, paper, polymer, or various other materials that will serve to retain and/or collect a sample. The body 201 can be made of polymer, plastic, wood, metal, or various other materials. The pad 206 is positioned on the heater 207. The heater 207 is attached to the body 201 by any suitable means such as thermoset, glue, or various other means of attachment.

The first reagent holder and dispenser 202 contains the first explosives detecting reagent 204 (reagent A) and the second reagent holder and dispenser 203 contains the second explosives detecting reagent 205 (reagent B). The reagent A contains Meisenheimer complexes. The reagent B provides a Griess reaction. The Meisenheimer complexes and Griess reaction are well known in the art and need not be described here.

The first reagent holder and dispenser 202 is positioned to deliver the first explosives detecting reagent (reagent A) 204 to the pad 206. The second reagent holder and dispenser 203 is positioned to deliver the second explosives detecting reagent (reagent B) 205 to the pad 206. The first and second reagent holders and dispensers 202 and 203 have openings 208 and 209 respectively that allow deliver of the first explosives detecting reagent (reagent A) 204 and the second explosives detecting reagent (reagent B) 205 to the pad 206. Instead of simple openings 208 and 209, the first and second reagent holders and dispensers 202 and 203 can have dispensing units such as needle valves. This type of dispensing vial is well know in the art and is readily availed for purchase from many suppliers.

The heater 207 is located beneath the pad 206 and in contact with the pad 206. The heater 207 is an electrical heater with a heating element extending in zig zag arrangements and electrical leads 210 and 211. The electrical leads 210 and 211 can be connected to an external battery 212 with corresponding lead holes 213 and 214. Other types of heaters can be used for the heater 207, such as chemical heaters. In another embodiment the heater 207 is a chemical heater and the electrical leads 210 and 211 and battery 212 are not included. The chemical heater 207 is well known in the art and need not be described here.

The structural details of embodiment of an explosives tester for explosives constructed in accordance with the present invention having been described the operation of the explosives tester 200 will now be considered. The explosives tester 200 uses a simple and rapid procedure summarized by the following four step operation:

STEP 1) A suspect surface is swiped with the pad 206. This will cause any explosives residue to be collected and held by the pad 206.

STEP 2) The dispensing vial 202 is used for dispensing reagent A 204 through opening 208 onto pad 206. The regent A 204 contacts any explosives residue that has been collected by pad 206. If the pad 207 becomes colored, the test is positive for explosives. If no color appears the test for explosives is negative to this point.

STEP 3) The heater 207 is activated. This causes the pad 207, reagent A 204, and any explosives residue to become heated. If the pad 207 now becomes colored, the test is positive for explosives. If no color appears the test for explosives is negative to this point.

STEP 4) The dispensing vial 203 is used for dispensing reagent B 205 through opening 209 onto pad 206. The regent B 205 contacts any explosives residue that has been collected by pad 206. If the pad 207 becomes colored, the test is positive for explosives. If no color appears the test for explosives is negative.

In one use of the explosives tester 200 provides a simple, chemical, field spot-test by to provide a rapid screen for the presence of a broad range of explosive residues. The explosives tester 200 is fast, extremely sensitive, low-cost, very easy to implement, and provides a very low rate of false positives. The explosives tester for explosives 200 provides a fast, sensitive, low-cost, very easy to implement system for testing the suspected packages. The explosives tester for explosives 200 is inexpensive and disposable. The explosives tester for explosives 200 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The explosives tester 200 is small enough that a number of them can fit in a pocket or brief case.

Figure 3:
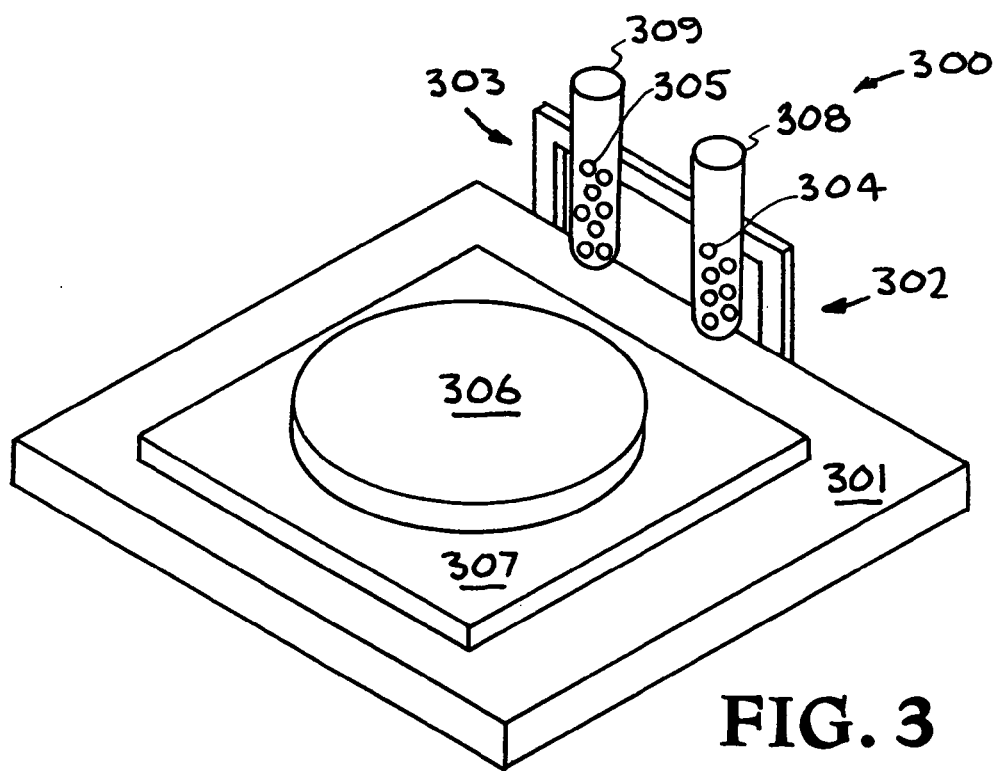
FIG. 3 illustrates another embodiment of an explosives tester constructed in accordance with the present invention.

Referring now to FIG. 3 another embodiment of an explosives tester for explosives constructed in accordance with the present invention is illustrated. This further embodiment is designated generally by the reference numeral 300. The explosives tester 300 comprises a body 301 with a sample collection unit 306 operatively connected to the body 301. A first explosives detecting reagent 304 (reagent A) is contained in a first reagent holder and dispenser 302 that is operatively connected to the body 301 and the sample collection unit 306. The first reagent holder and dispenser 302 containing the first explosives detecting reagent 304 is positioned to deliver the first explosives detecting reagent 304 to the sample collection unit 306. A second explosives detecting reagent 305 (reagent B) is contained in a second reagent holder and dispenser 303 operatively connected to the body 301 and the sample collection unit 306. The second reagent holder and dispenser 303 containing the second explosives detecting reagent 305 is positioned to deliver the second explosives detecting reagent 303 to the sample collection unit 306. A heater 307 is operatively connected to the sample collection unit 306.

The sample collection unit in the embodiment 300 comprises a disk shaped cotton pad 306 that is attached to the body 301. The pad 306 can be made of cotton, paper, polymer, or various other materials that will serve to retain and/or collect a sample. The body 301 can be made of polymer, plastic, wood, metal, or various other materials. The pad 306 is positioned on the heater 307. The heater 307 is attached to the body 301 by any suitable means such as thermoset, glue, or various other means of attachment.

The first reagent holder and dispenser 302 contains the first explosives detecting reagent 304 (reagent A) and the second reagent holder and dispenser 303 contains the second explosives detecting reagent 305 (reagent B). The reagent A contains Meisenheimer complexes. The reagent B provides a Griess reaction. The Meisenheimer complexes and Griess reaction are well known in the art and need not be described here.

The first reagent holder and dispenser 302 is positioned to deliver the first explosives detecting reagent (reagent A) 304 to the pad 306. The second reagent holder and dispenser 303 is positioned to deliver the second explosives detecting reagent (reagent B) 305 to the pad 306. The first and second reagent holders and dispensers 302 and 303 have openings 308 and 309 respectively that allow deliver of the first explosives detecting reagent (reagent A) 304 and the second explosives detecting reagent (reagent B) 305 to the pad 306. Instead of simple openings 308 and 309, the first and second reagent holders and dispensers 302 and 303 can have dispensing units such as needle valves. This type of dispensing vial is well know in the art and is readily available for purchase from many suppliers.

The heater 307 is located beneath the pad 306 and in contact with the pad 306. The heater 307 is a chemical heater. Chemical heaters, such as heater 307, are well known in the art and need not be described here.

The structural details of embodiment of an explosives tester for explosives constructed in accordance with the present invention having been described the operation of the explosives tester 300 will now be considered. The explosives tester 300 uses a simple and rapid procedure summarized by the following four step operation:

STEP 1) A suspect surface is swiped with the pad 306. This will cause any explosives residue to be collected and held by the pad 306.

STEP 2) The dispensing vial 302 is used for dispensing reagent A 304 through opening 308 onto pad 306. The regent A 304 contacts any explosives residue that has been collected by pad 306. If the pad 307 becomes colored, the test is positive for explosives. If no color appears the test for explosives is negative to this point.

STEP 3) The heater 307 is activated. This causes the pad 307, reagent A 304, and any explosives residue to become heated. If the pad 307 now becomes colored, the test is positive for explosives. If no color appears the test for explosives is negative to this point.

STEP 4) The dispensing vial 303 is used for dispensing reagent B 305 through opening 309 onto pad 306. The regent B 305 contacts any explosives residue that has been collected by pad 306. If the pad 307 becomes colored, the test is positive for explosives. If no color appears the test for explosives is negative.

Figure 4:
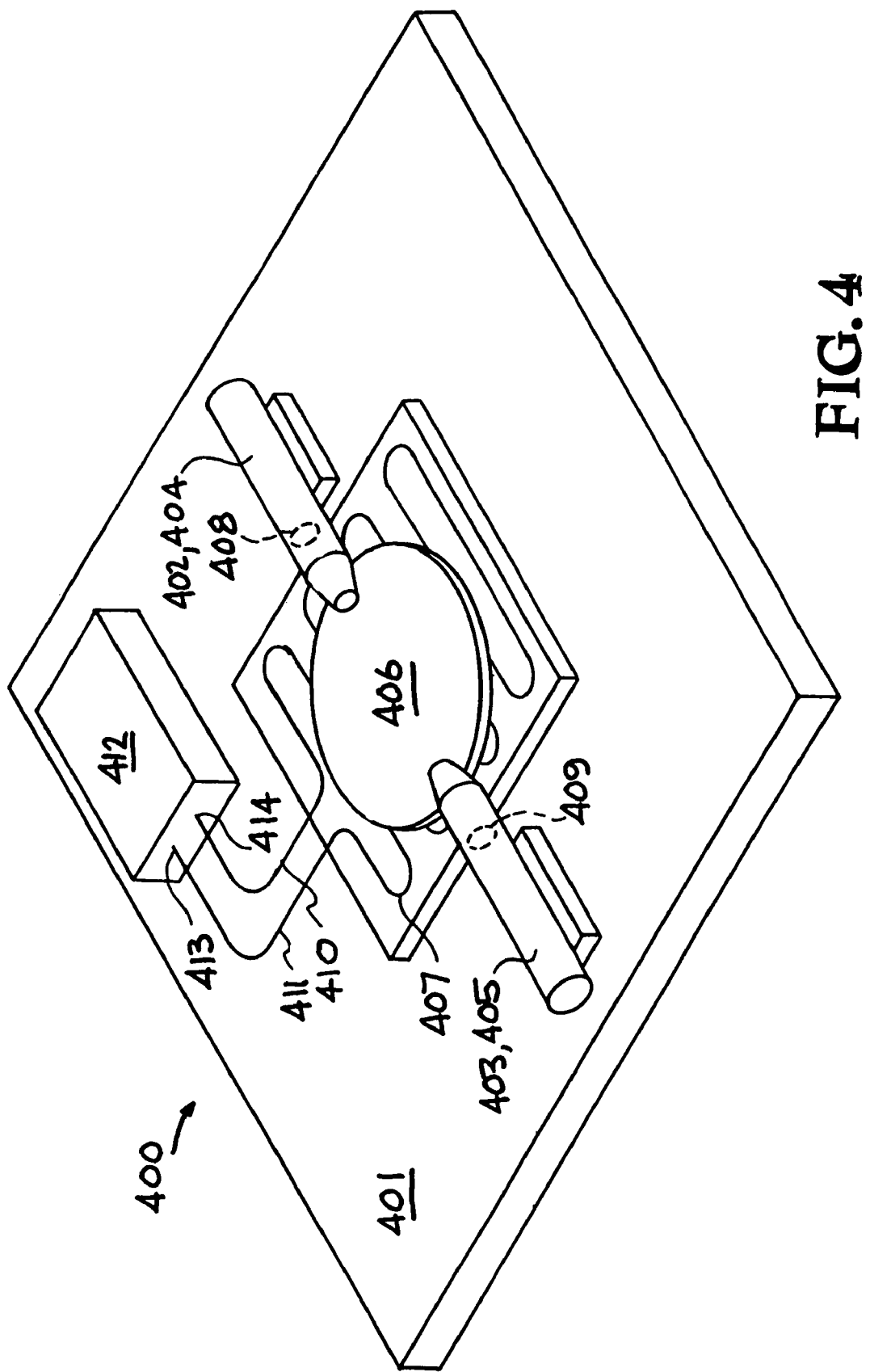
FIG. 4 illustrates yet another embodiment of an explosives tester constructed in accordance with the present invention.

In one use of the explosives tester 300 provides a simple, chemical, field spot-test by to provide a rapid screen for the presence of a broad range of explosive residues. The explosives tester 300 is fast, extremely sensitive, low-cost, very easy to implement, and provides a very low rate of false positives. The explosives tester for explosives 300 provides a fast, sensitive, low-cost, very easy to implement system for testing the suspected packages. The explosives tester for explosives 300 is inexpensive and disposable. The explosives tester for explosives 300 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The explosives tester 300 is small enough that a number of them can fit in a pocket or brief case. Referring now to FIG. 4 yet another embodiment of an inspection tester for explosives constructed in accordance with the present invention is illustrated. This further embodiment is designated generally by the reference numeral 400. The inspection tester 400 comprises a body 401 with a sample pad 406 operatively connected to the body 401. A first explosives detecting reagent 404 (reagent A) is contained in a first reagent holder and dispenser 402 that is operatively connected to the body 401 and the sample pad 406. The first reagent holder and dispenser 402 containing the first explosives detecting reagent 404 is positioned to deliver the first explosives detecting reagent 404 to the sample pad 406. A second explosives detecting reagent 405 (reagent B) is contained in a second reagent holder and dispenser 403 operatively connected to the body 401 and the sample pad 406. The second reagent holder and dispenser 403 containing the second explosives detecting reagent 405 is positioned to deliver the second explosives detecting reagent 403 to the sample pad 406. A heater 407 is operatively connected to the sample pad 406.

The sample pad in the embodiment 400 comprises a disk shaped cotton pad 406 that is attached to the body 401. The pad 406 can be made of cotton, paper, polymer, or various other materials that will serve to retain and/or collect a sample. The body 401 can be made of polymer, plastic, wood, metal, or various other materials. The pad 406 is attached to the body 401 by any suitable means such as thermoset, glue, or various other means of attachment.

The first reagent holder and dispenser 402 contains the first explosives detecting reagent 404 (reagent A) and the second reagent holder and dispenser 403 contains the second explosives detecting reagent 405 (reagent B). The reagent A contains Meisenheimer complexes. The reagent B provides a Griess reaction. The Meisenheimer complexes and Griess reaction are well known in the art and need not be described here.

The first reagent holder and dispenser 402 is positioned to deliver the first explosives detecting reagent (reagent A) 404 to the pad 406. The second reagent holder and dispenser 403 is positioned to deliver the second explosives detecting reagent (reagent B) 405 to the pad 406. The first and second reagent holders and dispensers 402 and 403 are squeezable vials with internal valves 408 and 409 respectively that deliver the first explosives detecting reagent (reagent A) 404 and the second explosives detecting reagent (reagent B) 405 to the pad 406. This type of squeezable vial is well know in the art and is readily availed for purchase from many suppliers.

The heater 407 is located beneath the pad 406 and in contact with the pad 406. The heater 407 is an electrical heater with a heating element extending in zig zag arrangements and electrical leads 410 and 411. The electrical leads 410 and 411 can be connected to an external battery 412 with corresponding lead holes 413 and 414. Other types of heaters can be used for the heater 407, such as chemical heaters.

The structural details of embodiment of an inspection tester for explosives constructed in accordance with the present invention having been described the operation of the inspection tester 400 will now be considered. The inspection tester 400 uses a simple and rapid procedure summarized by the following four step operation:

STEP 1) A suspect surface is swiped with the pad 406. This will cause any explosives residue to be collected and held by the pad 406.

STEP 2) The squeezable vial 402 is pressed dispensing reagent A 404 through internal valve 408 onto pad 406. The regent A 404 contacts any explosives residue that has been collected by pad 406. If the pad 407 becomes colored, the test is positive for explosives. If no color appears the test for explosives is negative to this point.

STEP 3) The heater 407 is activated. This causes the pad 407, reagent A 404, and any explosives residue to become heated. If the pad 407 now becomes colored, the test is positive for explosives. If no color appears the test for explosives is negative to this point.

STEP 4) The squeezable vial 403 is pressed dispensing reagent B 405 through internal valve 409 onto pad 406. The regent B 405 contacts any explosives residue that has been collected by pad 406. If the pad 407 becomes colored, the test is positive for explosives. If no color appears the test for explosives is negative.

In one use of the inspection tester 400 provides a simple, chemical, field spot-test by to provide a rapid screen for the presence of a broad range of explosive residues. The inspection tester 400 is fast, extremely sensitive, low-cost, very easy to implement, and provides a very low rate of false positives. The inspection tester for explosives 400 provides a fast, sensitive, low-cost, very easy to implement system for testing the suspected packages. The inspection tester for explosives 400 is inexpensive and disposable. The inspection tester for explosives 400 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 400 is small enough that a number of them can fit in a pocket or brief case.

Figure 5:
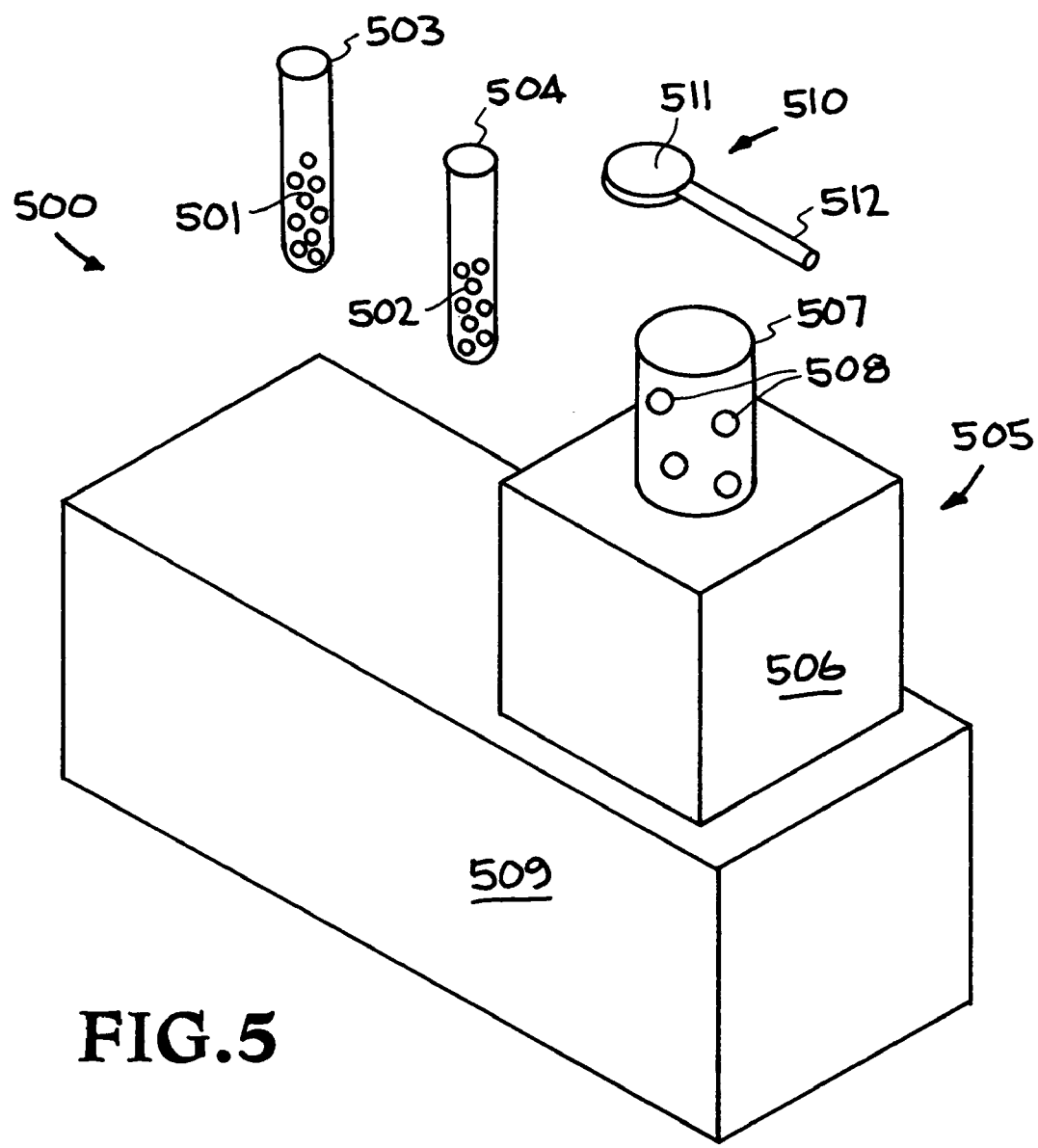
FIG. 5 illustrates another embodiment of an explosives tester constructed in accordance with the present invention.

Referring now to FIG. 5 of the drawings, an illustration of another embodiment of an explosives tester constructed in accordance with the present invention is illustrated. This embodiment of the explosives tester is designated generally by the reference numeral 500. The explosives tester 500 comprises a first explosives detecting reagent 501, a first reagent holder and dispenser 503, a second explosives detecting reagent 502, a second reagent holder and dispenser 504, containing said second explosives detecting reagent, a sample collection unit 510, and a dryer 505 for receiving said sample collection unit 510. The first reagent holder and dispenser 503 contains and dispenses the first explosives detecting reagent 501. The second reagent holder and dispenser 504 contains and dispenses the second explosives detecting reagent 502. The dryer 505 is positioned on a battery pack 509 that provides electrical power for the dryer 505. The dryer 505 includes a blower 506 and a receiving unit 507 for receiving the sample collection unit 510. Holes 508 in the receiving unit 507 provide vents for the air produced by blower 506. Other types of dryers can be used for the dryer 506. Dryers are well known in the art and need not be described here.

The structural details of embodiment of an explosives tester 500 for explosives constructed in accordance with the present invention having been described, the operation of the explosives tester 500 will now be considered. The explosives tester 500 uses a simple and rapid procedure summarized by the following four step operation:

STEP 1) A sample collection unit 510 is exposed to the suspect substance. This may be accomplished by the sample collection unit 510 being swiped across a surface containing the suspect substance or the sample collection unit 510 may be exposed to the suspect substance in other ways such as adding the suspect substance to the sample collection unit 510.

STEP 2) The first explosives detecting reagent 501 from first reagent holder and dispenser 503 is deposited onto the sample collection unit 510 with the suspect substance. If the sample collection unit 510 becomes colored, it's positive for explosives. If no color appears then the additional steps are performed.

STEP 3) The dryer 505 is activated. The sample collection unit 510 is positioned in the receiving unit 507. The blower 506 blows air across the sample collection unit 510. If a color appears on the sample collection unit 510, it's positive for explosives. If no color appears then the additional step is performed.

STEP 4) The second explosives detecting reagent 502 from second reagent holder and dispenser 504 is deposited onto the sample collection unit 510 with the suspect substance. If the sample collection unit 510 becomes colored, it's positive for explosives. If no color appears then the test is negative for explosives.

Optional Additional Step—The dryer 505 is activated. The sample collection unit 510 after is has been exposed to the second explosives detecting reagent 502 is positioned in the receiving unit 507. The blower 506 blows air across the sample collection unit 510. If a color appears on the sample collection unit 510, it's positive for explosives. If no color appears then the test is negative for explosives.

The particular embodiment of the explosives tester 500 uses reagents depending on the type of explosives present, the chemistry reaction scheme, the types of chemicals, the concentrations, the quantity, and the heat. A large number of common military and industrial explosives can be easily detected such as HMX, RDX, NG, TATB, Tetryl, PETN, TNT, DNT, TNB, DNB and NC. Many more compounds are being added to this list.

The explosives tester 500 is fast, sensitive, and is easy to implement. The explosives tester 500 can be used virtually anywhere, car portal checkpoints, airports, first responders, Federal, State, and local agencies. The explosives tester 500 can be used as a primary screening tool by non technical personnel to determine whether a surface contains explosives. Explosive Ordinance Disposal teams cannot simply explode suspect packages for concerns of disbursing radioactive material, biological agents, or chemical agents.

The particular embodiment of an explosives tester 500 will now be described in greater detail. As shown in FIG. 5 a swab 511 is attached to one end of a pencil sized wand 512 to provide the sample collection unit 510. The other end of the wand 512 serves as a handle. The swab 511 can be made of cotton, paper, polymer, or various other materials that will serve to retain and/or collect a sample. The wand 512 can be made of plastic, wood, metal, or various other materials. The swab 511 is attached to the wand by any suitable means such as glue, heating, crimping or various other means of attachment to provide the sample collection unit 510.

The sample collection unit is exposed to the first explosives detecting reagent 501. The first explosives detecting reagent 501 contains Meisenheimer complexes. Subsequently the sample collection unit 510 is exposed to the second explosives detecting reagent 502. The second explosives detecting reagent 502 provides a Griess reaction. The Meisenheimer complexes and Griess reaction are well known in the art and need not be described here.

The explosives testers 500 can be stored and carried in a case. The explosives tester for explosives 500 can be used virtually anywhere, car portal checkpoints, airports, first responders, Federal, State, and local agencies. A large number of common military and industrial explosives can be easily detected such as HMX, RDX, NG, TATB, Tetryl, PETN, TNT, DNT, TNB, DNB and NC.

Figure 6:
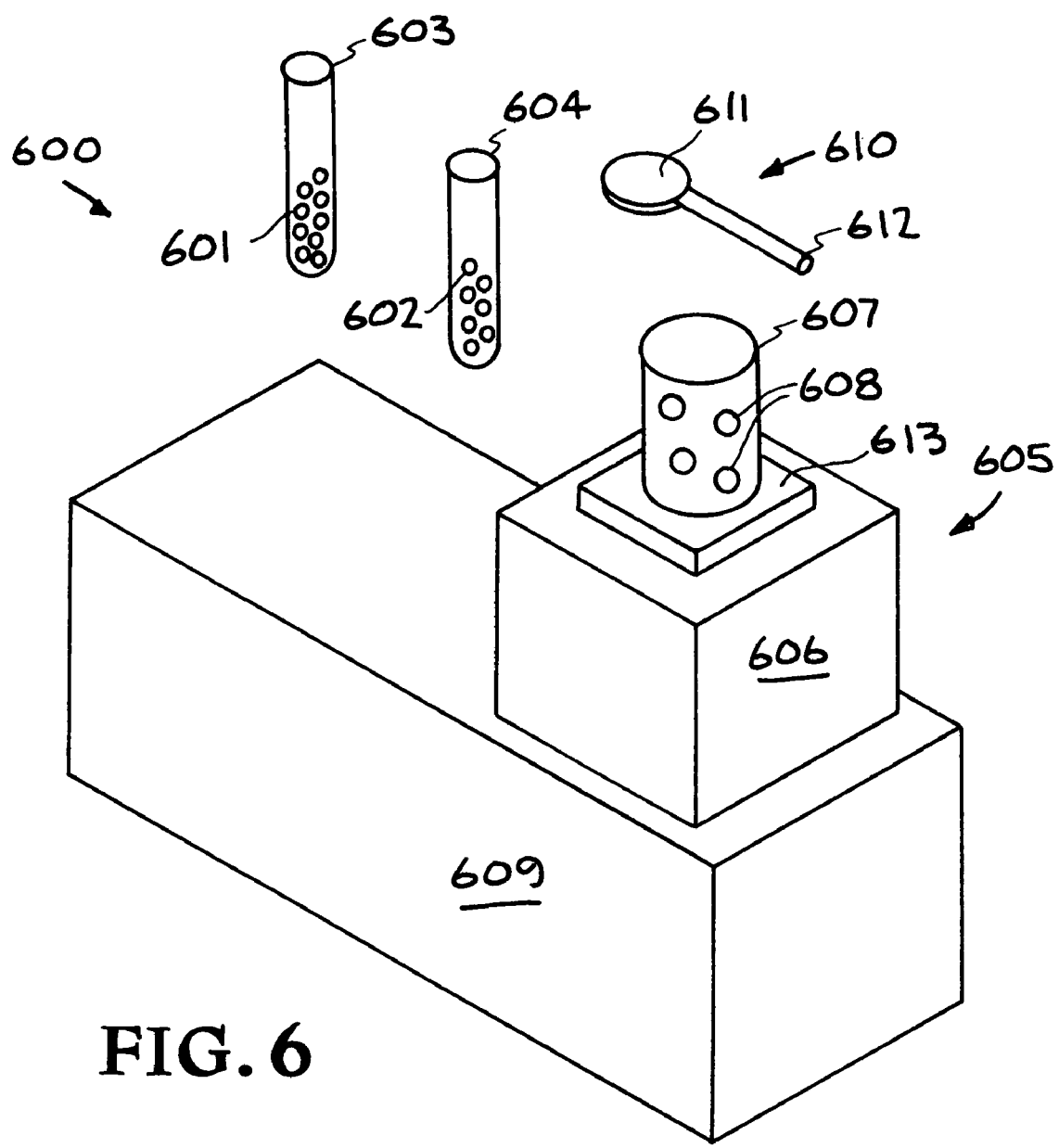
FIG. 6 illustrates another embodiment of an explosives tester constructed in accordance with the present invention.

Referring now to FIG. 6 of the drawings, an illustration of yet another embodiment of an explosives tester constructed in accordance with the present invention is illustrated. This embodiment of the explosives tester is designated generally by the reference numeral 600. The explosives tester 600 comprises a first explosives detecting reagent 601, a first reagent holder and dispenser 603, a second explosives detecting reagent 602, a second reagent holder and dispenser 604, containing said second explosives detecting reagent, a sample collection unit 610, and a dryer 605 for receiving said sample collection unit 610. The first reagent holder and dispenser 603 contains and dispenses the first explosives detecting reagent 601. The second reagent holder and dispenser 604 contains and dispenses the second explosives detecting reagent 602. The dryer 605 is positioned on a battery pack 609 that provides electrical power for the dryer 605. The dryer 605 includes a blower 606, a heating unit 611 and a receiving unit 607 for receiving the sample collection unit 610. Holes 608 in the receiving unit 607 provide vents for the heated air produced by blower 606 and heating unit 611. Other types of dryers can be used for the dryer 606. Dryers with heaters are well known in the art and need not be described here.

The structural details of embodiment of an explosives tester 600 for explosives constructed in accordance with the present invention having been described, the operation of the explosives tester 600 will now be considered. The explosives tester 600 uses a simple and rapid procedure summarized by the following four step operation:

STEP 1) A sample collection unit 610 is exposed to the suspect substance. This may be accomplished by the sample collection unit 610 being swiped across a surface containing the suspect substance or the sample collection unit 610 may be exposed to the suspect substance in other ways such as adding the suspect substance to the sample collection unit 610.

STEP 2) The first explosives detecting reagent 601 from first reagent holder and dispenser 603 is deposited onto the sample collection unit 610 with the suspect substance. If the sample collection unit 610 becomes colored, it's positive for explosives. If no color appears then the additional steps are performed.

STEP 3) The dryer 605 is activated. The sample collection unit 610 is positioned in the receiving unit 607. The blower 606 and heating unit 611 blows hot air across the sample collection unit 610. If a color appears on the sample collection unit 610, it's positive for explosives. If no color appears then the additional step is performed.

STEP 4) The second explosives detecting reagent 602 from second reagent holder and dispenser 604 is deposited onto the sample collection unit 610 with the suspect substance. If the sample collection unit 610 becomes colored, it's positive for explosives. If no color appears then the test is negative for explosives.

Optional Additional Step—The dryer 605 is activated. The sample collection unit 610 after is has been exposed to the second explosives detecting reagent 602 is positioned in the receiving unit 607. The blower 606 and heating unit 611 blows hot air across the sample collection unit 610. If a color appears on the sample collection unit 610, it's positive for explosives. If no color appears then the test is negative for explosives.

The particular embodiment of the explosives tester 600 uses reagents depending on the type of explosives present, the chemistry reaction scheme, the types of chemicals, the concentrations, the quantity, and the heat. A large number of common military and industrial explosives can be easily detected such as HMX, RDX, NG, TATB, Tetryl, PETN, TNT, DNT, TNB, DNB and NC. Many more compounds are being added to this list.

The explosives tester 600 is fast, sensitive, and is easy to implement. The explosives tester 600 can be used virtually anywhere, car portal checkpoints, airports, first responders, Federal, State, and local agencies. The explosives tester 600 can be used as a primary screening tool by non technical personnel to determine whether a surface contains explosives.

Explosive Ordinance Disposal teams cannot simply explode suspect packages for concerns of disbursing radioactive material, biological agents, or chemical agents.

The particular embodiment of an explosives tester 600 will now be described in greater detail. As shown in FIG. 6 a swab 611 is attached to one end of a pencil sized wand 612 to provide the sample collection unit 610. The other end of the wand 612 serves as a handle. The swab 611 can be made of cotton, paper, polymer, or various other materials that will serve to retain and/or collect a sample. The wand 612 can be made of plastic, wood, metal, or various other materials. The swab 611 is attached to the wand by any suitable means such as glue, heating, crimping or various other means of attachment to provide the sample collection unit 610.

The sample collection unit is exposed to the first explosives detecting reagent 601. The first explosives detecting reagent 601 contains Meisenheimer complexes. Subsequently the sample collection unit 610 is exposed to the second explosives detecting reagent 602. The second explosives detecting reagent 602 provides a Griess reaction. The Meisenheimer complexes and Griess reaction are well known in the art and need not be described here.

The explosives testers 600 can be stored and carried in a case. The explosives tester for explosives 600 can be used virtually anywhere, car portal checkpoints, airports, first responders, Federal, State, and local agencies. A large number of common military and industrial explosives can be easily detected such as HMX, RDX, NG, TATB, Tetryl, PETN, TNT, DNT, TNB, DNB and NC.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A tester for testing for explosives associated with a test location, comprising:
a tester body;
a first reagent for detecting explosives;
a first reagent container for receiving said first reagent means;
a second reagent for detecting explosives;
a second reagent container for receiving said second reagent means;
a flat disk sample collection pad for exposure to said test location, exposure to said first explosives detecting reagent, and exposure to said second explosives detecting reagent, said flat disk sample collection pad operatively connected to said tester body,
wherein said first reagent container is operatively connected to said body and positioned to deliver said first reagent to said flat disk sample collection pad,
wherein said second reagent container is operatively connected to said body and positioned to deliver said second reagent to said flat disk sample collection pad; and
an environmental means for receiving said flat disk sample collection pad, said environmental means being a heater or a dryer operatively connected to said tester body for heating or drying said flat disk sample collection pad and testing the test location for the explosives.

2. The tester of claim 1 wherein said environmental means is a heater.

3. The tester of claim 1 wherein said environmental means is a dryer.

4. The tester of claim 1 wherein said environmental means is a heater and dryer.

5. The tester of claim 1 wherein said environmental means is a chemical heater.

6. The tester of claim 1 wherein said environmental means is an electric heater.

7. The tester of claim 6 including a heating pad.

8. The tester of claim 6 including a receiving unit for receiving said flat disk sample collection pad.

9. The tester of claim 6 including a heating pad and a receiving unit for receiving said flat disk sample collection pad.

10. The tester of claim 6 including a battery for providing power to said heater.

11. The tester of claim 6 including a switch for controlling said heater.

12. The tester of claim 6 including a battery for providing power to said heater and a switch for controlling said heater.

* * * * *